US008470318B2

(12) United States Patent
Ravetch et al.

(10) Patent No.: US 8,470,318 B2
(45) Date of Patent: Jun. 25, 2013

(54) POLYPEPTIDES WITH ENHANCED ANTI-INFLAMMATORY AND DECREASED CYTOTOXIC PROPERTIES AND RELATING METHODS

(75) Inventors: Jeffrey V. Ravetch, New York, NY (US); Falk Nimmerjahn, Thurnau (DE); Yoshikatsu Kaneko, Niigata (JP)

(73) Assignee: The Rockefeller University, New York, NY (US)

( * ) Notice: Subject to any disclaimer, the term of this patent is extended or adjusted under 35 U.S.C. 154(b) by 518 days.

(21) Appl. No.: 12/447,204

(22) PCT Filed: Jul. 3, 2007

(86) PCT No.: PCT/US2007/072771
§ 371 (c)(1),
(2), (4) Date: Feb. 18, 2010

(87) PCT Pub. No.: WO2008/057634
PCT Pub. Date: May 15, 2008

(65) Prior Publication Data
US 2010/0189714 A1    Jul. 29, 2010

Related U.S. Application Data

(63) Continuation-in-part of application No. PCT/US2007/008396, filed on Apr. 3, 2007, which is a continuation of application No. PCT/US2006/041791, filed on Oct. 27, 2006.

(60) Provisional application No. 60/789,384, filed on Apr. 5, 2006, provisional application No. 60/734,196, filed on Nov. 7, 2005.

(51) Int. Cl.
*A61K 39/395* (2006.01)
*A61K 47/00* (2006.01)
*C07K 16/00* (2006.01)

(52) U.S. Cl.
USPC ............... 424/130.1; 424/172.1; 424/173.1; 424/278.1

(58) Field of Classification Search
None
See application file for complete search history.

(56) References Cited

U.S. PATENT DOCUMENTS

| | | | |
|---|---|---|---|
| 4,719,107 | A | 1/1988 | Carosella et al. |
| 6,156,881 | A | 12/2000 | Seed et al. |
| 6,391,507 | B1 | 5/2002 | Macholdt |
| 6,656,466 | B1 | 12/2003 | Etcheverry et al. |
| 7,064,191 | B2 | 6/2006 | Shinkawa |
| 7,427,469 | B2 | 9/2008 | Amara et al. |
| 2002/0164328 | A1* | 11/2002 | Shinkawa et al. ......... 424/130.1 |
| 2004/0202658 | A1* | 10/2004 | Benyunes ................. 424/144.1 |
| 2005/0123546 | A1 | 6/2005 | Umana |
| 2005/0181359 | A1* | 8/2005 | Optelten et al. .................. 435/5 |
| 2006/0030521 | A1 | 2/2006 | DeFrees et al. |
| 2007/0041979 | A1 | 2/2007 | Raju et al. |
| 2007/0048740 | A1 | 3/2007 | Isogai et al. |
| 2008/0025913 | A1 | 1/2008 | Bowdish et al. |
| 2008/0206246 | A1 | 8/2008 | Ravetch et al. |
| 2009/0004179 | A1 | 1/2009 | Ravetch |

FOREIGN PATENT DOCUMENTS

| | | |
|---|---|---|
| EA | 200870411 A1 | 4/2009 |
| EP | 0666757 A1 | 8/1995 |
| EP | 1020528 A2 | 7/2000 |
| WO | 9639488 A1 | 12/1996 |
| WO | 0063403 A2 | 10/2000 |
| WO | 0230954 A1 | 4/2002 |
| WO | 0240047 A2 | 5/2002 |
| WO | 2004058944 A2 | 7/2004 |
| WO | 2005063808 A1 | 7/2005 |
| WO | 2007005786 A2 | 1/2007 |
| WO | 2007055916 A2 | 5/2007 |
| WO | 2007117505 A1 | 10/2007 |
| WO | 2008057634 A2 | 5/2008 |
| WO | 2009079382 | 6/2009 |
| WO | 2009086262 A1 | 7/2009 |

OTHER PUBLICATIONS

Brekke et al. Nature Reviews Drug Discovery. Jan. 2003, 2:52-62.*
Firestein. Nature May 15, 2003, 423:356-361.*
Burton et al. Science 2006 313:627-628.*
Jefferis. Nature Biotechnology. 2006 24;10:1230-1231.*
Kaveri et al. The New England Journal of Medicine. 2008, 359;3:307-309.*
Office Action issued on Jan. 20, 2010 for U.S. Appl. No. 12/013,212.
Raju et al., Glycoengineering of therapeutic glycoproteins: In vitro galactosylation and sialylation of glycoproteins with terminal N-Acetylglucosamine and galactose residues, Biochemistry 2001, 40, 8868-8876.
Ravetch et al., "IgG Fc Receptors," Annu. Rev. immunol. 2001. 19:275-90.
Vitetta et al., "Considering Therapeutic Antibodies," Science (2006) 313:308-309.
Jin et al., "Protection against rat endotoxic shock by p55 tumor necrosis factor (TNF) receptor immunoadhesin: comparison with anti-TNF monoclonal antibody," J. Infect. Dis. (1994) 170(5):1323-1326.
Kaneko et al., "Anti-Inflammatory Activity of Immunoglobulin G Resulting from FC Sialylation," Science (Aug. 1, 2006); vol. 313, No. 5787; pp. 670-673.
Anthony et al., "Recapitulation of IVIG anti-inflammatory activity with recombinant IgC Fc," Science (Apr. 2008); vol. 320, No. 5874; pp. 373-376.
Jassal et al., "Sialylation of Human IgC-FC Carbohydrate by Transfected Rat alpha2,6-sialyltransferase," Biochem. and Biophys. Res. Comm. (2001); vol. 286; pp. 243-249.
Scallon et al., "Niger levels of sialylated Fc glycans in immunoglobulin G molecules can adversely impact functionality," Mol. Immunol. (2007); vol. 44, No. 7; pp. 1524-1534.

(Continued)

*Primary Examiner* — Chun Dahle
(74) *Attorney, Agent, or Firm* — Fox Rothschild LLP; Gerard P. Norton; Jianming Jimmy Hao (57) ABSTRACT

The invention provides a polypeptide containing at least one IgG Fc region, wherein said at least one IgG Fc region is glycosylated with at least one galactose moiety connected to a respective terminal sialic acid moiety by a α 2, 6 linkage, and wherein said polypeptide having a higher anti-inflammatory activity as compared to an unpurified antibody.

7 Claims, 5 Drawing Sheets

OTHER PUBLICATIONS

Raju et al., "Glycoengineering of therapeutic glycoproteins: In vitro galactosylation and sialylation of glycoproteins with terminal N-acetylglucosamine and galactose residues," Biochemistry (2001); vol. 40; pp. 8868-8876.

Dalziel et al., "Lectin analysis of 24 human immunoglobulin G N-glycan sialylation," Glycoconjugate J. (1999); vol. 16; pp. 801-807.

Wang et al., "The immobilized leukoagglutinin from the seeds of maackia-amurensis binds with high affinity to complex-type asn-linked oligosaccharides containing sialic acid-linked alpha-2 3 to penultimate galactose residues," J. Biol. Chem. (1988); vol. 263, No. 10; pp. 4576-4585.

Nimmerjahn et al., "The anti-inflammatory activity of IgC; the intravenous IgC paradox," J. Exp. Med. (Jan. 2007); vol. 204, No. 1; pp. 11-15.

Weikert et al., "Engineering Chinese Hamster Ovary Cells to Maximize Sialic Acid Content of Recombinant Glycoproteins," Nature Biotech. (Nov. 1999); vol. 17; pp. 1116-1121.

Stadlmann et al., "A close look at human IgG sialylation and subclass distribution after lectin fractionation," Proteomics (2009): vol. 9; pp. 4143-4153.

Kemminer et al., "Production of Molecular Characterization of Clinical Phase I Anti-melanoma Mouse IgG3 Monoclonal Antibody R24," Biotechnol. Prog. (2001); vol. 17, pp. 809-821.

Stadlmann et al., "Analytical and functional aspects of antibody sialylation," J Clin Immunol (published online: Apr. 14, 2010).

Hodges et al., "Activatin of the lectin DC-Sign induces an immature dendritic cell phenotype triggering Rho-GTPase activity required for HIV-1 replication," Nature Immunology (2007); vol. 8, pp. 569-570.

Caparros, et al., "DC-Sign litigation on dendritic cells results in ERK an dP13k activation and modulates cytokine production," Blood (2006); vol. 107: pp. 3950-3958.

Elomaa et al., "Cloning of a novel bacteria-binding receptor structurally relatd to scavenger receptors and expressed in a subset of macrophages," Cell (1995); vol. 80: pp. 603-609.

Galustian et al., High and low affinity carbohydrate ligands revealed for murine SIGN-R1 by carbohydrate array and cell binding approaches, and differing specificities for SIGN-R3 and langerin, International Immunology (May 2004); vol. 16, pp. 853-867, The Japanese Society for Immunology, Japan.

Tailleux et al., "DC-sign is the major mycobacterium tuberculosis reeptor on human dendiritic cells," Journal of Experimental Medicine (Jan. 2003); vol. 197, pp. 121-127, The Rockefeller University Press, USA.

Pohlmann et al., "Hepatitis C virus glycoproteins interact with DC-sign and DC-SIGNR," Journal of Virology (Apr. 2003); vol. 77, pp. 4070-40/80, American Society for Microbiology, USA.

Geijtenbeck et al., "Identifrication of DC-SIGN, a novel dendritic cell-specific ICAM-3 receptor that supports primary immune response," Cell (Mar. 2000); vol. 100, pp. 575-585, Cell Press, USA.

Takai et al., "The study of allergy by Japanese researchers: a historical perspective," International Immunology (1996); vol. 21, No. 12, pp. 1311-1316, The Japanese Society for Immunology, Japan.

Lanoue et al., "Sign-R1 contributes to protection against lethal pneumococcal infection in mice," Journal of Experimental Medicine (Dec. 2004); vol. 200, No. 11, pp. 1383-1393, The Rocekfeller University Press, USA.

Kang et al., "A dominant compelment fixation pathway for pneumococcal polysaccharides initiated by SIGN-R1 interacting with C1q," Cell (2006); vol. 125, pp. 47-58.

Van Der Laan et al., "Regulation and functional involvment of macrophage scavenger receptor MARCO in clearance of bacteria in vivo," The Journal of Immunology (1999); vol. 162, No. 2, pp. 939-947.

Requena et al., "inhibition of IV-1 transmission in trans from dendritic cells to CD4+ T lymphocytes by natural antibodies to the CRD domain of DC-SIGN purified from breast milk and intravenous immunoglobulins," Immunology (2008); vol. 123, No. 4, pp. 508-518.

Boruchov et al., "Activating and inhibitory IgG Fc receptors on human DCs mediate opposing functions," The Journal of Clinical Investigation (2005); vol. 115, No. 10, pp. 2914-2923.

Higuchi et al., "Characterization of the rabbit hmolog of human MUC1 glycoprotein isolated from bladder by affinity chromatography on immobilized jacalin," Gycobiology (2000); vol. 10, No. 7, pp. 659-667.

Qiu et al., "Use of multidimensional lectin affinity chromatography in differential glycoproteomics," Analytical Chemistry (2005); vol. 77, No. 9, pp. 2802-2809.

Office Action issued on Mar. 18, 2010 for U.S. Appl. No. 12/428,402.

International Search Report issued on Aug. 29, 2007 for International Application No. PCT/US06/41791.

Office Action issued on Jan. 20, 2011 for U.S. Appl. No. 12/013,212.

Extended European Search Report issued on Apr. 14, 2010 for European Application No. 07812601.8.

International Search Report issued on Aug. 8, 2008 for International Application No. PCT/US07/08396.

International Search Report issued on Mar. 16, 2009 for International Application No. PCT/US08/86622.

International Search Report issued on Aug. 8, 2008 for International Application No. PCT/US08/72771.

Extended European Search Report issued on Apr. 9, 2010 for European Application No. 07754846.9.

Office Action issued on Jun. 29, 2010 for U.S. Appl. No. 11/957,015.

Office Action issued on Mar. 24, 2010 for U.S. Appl. No. 11/957,015.

* cited by examiner

POLYPEPTIDES WITH ENHANCED ANTI-INFLAMMATORY AND DECREASED CYTOTOXIC PROPERTIES AND RELATING METHODS

CROSS REFERENCE TO RELATED APPLICATIONS

This application is a National Stage filing under 35 U.S.C. §371(c) of International application Ser. No. PCT/US07/72771 filed Jul. 3, 2007. PCT/US07/72771 is a continuation-in-part patent application of PCT Patent Application Number PCT/US07/08396, filed on Apr. 3, 2007, which claims the benefit of U.S. Provisional Patent Application No. 60/789,384, filed on Apr. 5, 2006, both of which are incorporated herein by reference. PCT/US07/72771 also claims the benefit of PCT Patent Application Number PCT/US06/41791, filed on Oct. 27, 2006, and U.S. Provisional Patent Application No. 60/734,196, filed on Nov. 7, 2005, both of which are also incorporated herein by reference.

STATEMENT REGARDING FEDERALLY FUNDED RESEARCH

The Research leading to the present invention was supported in part, by National Institutes of Health Grant No. AI 034662. Accordingly, the U.S. Government has certain rights in this invention.

FIELD OF THE INVENTION

The present invention relates to novel method for designing therapeutic polypeptides for treatment of inflammatory diseases.

BACKGROUND

Although cellular receptors for immunoglobulins were first identified nearly 40 years ago, their central role in the immune response was only discovered in the last decade. They are key players in both the afferent and efferent phase of an immune response, setting thresholds for B cell activation and antibody production, regulating the maturation of dendritic cells and coupling the exquisite specificity of the antibody response to effector pathways, such as phagocytosis, antibody dependent cellular cytotoxicity and the recruitment and activation of inflammatory cells. Their central role in linking the humoral immune system to innate effector cells has made them attractive immunotherapeutic targets for either enhancing or restricting the activity of antibodies in vivo.

The interaction of antibodies and antibody-antigen complexes with cells of the immune system effects a variety of responses, including antibody dependent cell-mediated cytotoxicity (ADCC) and complement dependent cytotoxicity (CDC), phagocytosis, inflammatory mediator release, clearance of antigen, and antibody half-life (reviewed in Daron, *Annu Rev Immunol*, 15, 203-234 (1997); Ward and Ghetie, *Therapeutic Immunol*, 2, 77-94 (1995); Ravetch and Kinet, *Annu Rev Immunol*, 9, 457-492 (1991)), each of which is incorporated herein by reference).

Antibody constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, and IgG4; IgA1 and IgA2. The heavy chain constant regions that correspond to the different classes of immunoglobulins are called $\alpha$, $\delta$, $\epsilon$, $\gamma$, and $\mu$, respectively. Of the various human immunoglobulin classes, human IgG1 and IgG3 mediate ADCC more effectively than IgG2 and IgG4.

Papain digestion of antibodies produces two identical antigen binding fragments, called Fab fragments, each with a single antigen binding site, and a residual "Fc" fragment, whose name reflects its ability to crystallize readily. The Fc region is central to the effector functions of antibodies. The crystal structure of the human IgG Fc region has been determined (Deisenhofer, *Biochemistry*, 20, 2361-2370 (1981), which is incorporated herein by reference). In human IgG molecules, the Fc region is generated by papain cleavage N-terminal to Cys, 226.

IgG has long been appreciated to mediate both pro- and anti-inflammatory activities through interactions mediated by its Fc fragment. Thus, while Fc-FcγR interactions are responsible for the pro-inflammatory properties of immune complexes and cytotoxic antibodies, intravenous gamma globulin (IVIG) and its Fc fragments are anti-inflammatory and are widely used to suppress inflammatory diseases. The precise mechanism of such paradoxical properties is unclear but it has been proposed that glycosylation of IgG is crucial for regulation of cytotoxicity and inflammatory potential of IgG.

IgG contains a single, N-linked glycan at $Asn^{297}$ in the CH2 domain on each of its two heavy chains. The covalently-linked, complex carbohydrate is composed of a core, biantennary penta-polysaccharide containing N-acetylglucosamine (GlcNAc) and mannose (man). Further modification of the core carbohydrate structure is observed in serum antibodies with the presence of fucose, branching GlcNAc, galactose (gal) and terminal sialic acid (sa) moieties variably found. Over 40 different glycoforms have thus been detected to be covalently attached to this single glycosylation site. Fujii et al., *J. Biol. Chem.* 265, 6009 (1990). Glycosylation of IgG has been shown to be essential for binding to all FcγRs by maintaining an open conformation of the two heavy chains. Jefferis and Lund, *Immune.l Lett*. 82, 57 (2002), Sondermann et al., *J. Mol. Biol*. 309, 737 (2001). This absolute requirement of IgG glycosylation for FcγR binding accounts for the inability of deglycosylated IgG antibodies to mediate in vivo triggered inflammatory responses, such as ADCC, phagocytosis and the release of inflammatory mediators. Nimmerjahn and Ravetch, *Immunity* 24, 19 (2006). Further observations that individual glycoforms of IgG may contribute to modulating inflammatory responses has been suggested by the altered affinities for individual FcγRs reported for IgG antibodies containing or lacking fucose and their consequential affects on cytotoxicity. Shields et al., *J. Biol. Chem.* 277, 26733 (2002), Nimmerjahn and Ravetch, *Science* 310, 1510 (2005). A link between autoimmune states and specific glycosylation patterns of IgG antibodies has been observed in patients with rheumatoid arthritis and several autoimmune vasculities in which decreased galactosylation and sialylation of IgG antibodies have been reported. Parekh et al., *Nature* 316, 452 (1985), Rademacher et al., *Proc. Natl. Acad. Sci. USA* 91, 6123 (1994), Matsumoto et al., 128, 621 (2000), Holland et al., Biochim. Biophys. Acta Dec 27; [Epub ahead of print] 2005. Variations in IgG glycoforms have also been reported to be associated with aging and upon immunization, although the in vivo significance of these alterations have not been determined. Shikata et al., *Glycoconj. J.* 15, 683 (1998), Lastra, et al., *Autoimmunity* 28, 25 (1998).

Accordingly, there is a need for the development of methods for the generation of polypeptides that would account for the disparate observations of IVIG properties in vivo.

SUMMARY OF INVENTION

The present invention fills the foregoing need by providing such methods and molecules. In one aspect, the invention provides an isolated polypeptide containing at least one IgG Fc region, having altered properties compared to an unpurified antibody preparation, wherein sialylation of the isolated polypeptide is higher than the sialylation of the unpurified antibody preparation. In one embodiment, the isolated polypeptide containing at least one IgG Fc region is glycosylated with at least one galactose moiety connected to a respective terminal sialic acid moiety by a α 2,6 linkage, and wherein said polypeptide having a higher anti-inflammatory activity as compared to an unpurified antibody. In one embodiment the isolated polypeptide containing at least one IgG Fc region is glycosylated with at least one galactose moiety connected to a respective terminal sialic acid moiety by a α 2,6 linkage, and wherein said polypeptide having a reduced binding to an Fc activating receptor as compared to an unpurified antibody preparation. In a further embodiment the Fc activating receptor is selected from the group consisting of FcγRIIA, FcγRIIC and FcγRIIIA.

In another aspect, the instant invention provides a pharmaceutical formulation comprising a polypeptide containing at least one Fc region having a higher anti-inflammatory activity, in combination with a suitable carrier or diluent.

A method of modulating properties of a polypeptide comprising an Fc region comprising altering the sialylation of the polysaccharide chain of the Fc region.

In one embodiment the method comprises: providing an unpurified source of the polypeptide containing at least one Fc region, said unpurified source of the polypeptide containing at least one Fc region comprising a plurality of the polypeptides containing at least one Fc region having a polysaccharide chain comprising a terminal sialic acid connected to a galactose moiety through a α 2,6 linkage, and a plurality of the polypeptides containing at least one Fc region lacking a polysaccharide chain comprising a terminal sialic acid connected to a galactose moiety through the α 2,6 linkage; and increasing the ratio of the plurality of the polypeptides containing at least one Fc region having the polysaccharide chain comprising the terminal sialic acid connected to the galactose moiety through the α 2,6 linkage to the plurality of the polypeptide containing at least one Fc region lacking the polysaccharide chain comprising the terminal sialic acid connected to the galactose moiety through the α 2,6 linkage.

DETAILED DESCRIPTION

The inventors have surprisingly found that the cytotoxic and anti-inflammatory response of the IgG Fc domain results from the differential sialylation of the Fc-linked core polysaccharide. The cytotoxicity of IgG antibodies is reduced upon sialylation; conversely, the anti-inflammatory activity of IVIG is enhanced. IgG sialylation is shown to be regulated upon the induction of an antigen-specific immune response, thus providing a novel means of switching IgG from an innate, anti-inflammatory molecule in the steady-state, to an adaptive, pro-inflammatory species upon antigenic challenge. The Fc-sialylated IgGs bind to a unique receptor on macrophages that in turn upregulates an inhibitory Fcγ receptor (FcγR) thereby protecting against autoantibody-mediated pathology. See, generally, Ravetch and Nimmerjahn, J. Experim. Medicine 24(1): 11-15 (2007).

Accordingly, the instant disclosure provides an advantageous strategy of creating and selecting IgGs with desired cytotoxic and anti-inflammatory potential.

Definitions

Throughout the present specification and claims, the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991), which is expressly incorporated herein by reference. The "EU index as in Kabat" refers to the residue numbering of the human IgG1 EU antibody.

The term "native" or "parent" refers to an unmodified polypeptide comprising an Fc amino acid sequence. The parent polypeptide may comprise a native sequence Fc region or an Fc region with pre-existing amino acid sequence modifications (such as additions, deletions and/or substitutions).

The term "polypeptide" refers to any fragment of a protein containing at least one IgG Fc region, including, without limitation, fully functional proteins, such as, for example, antibodies, e.g., IgG antibodies.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

The "CH2 domain" of a human IgG Fc region (also referred to as "CY2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain (Burton, *Mol Immunol*, 22, 161-206 (1985), which is incorporated herein by reference).

The "CH3 domain" comprises the stretch of residues C-terminal to a CH2 domain in an Fc region (i.e., from about amino acid residue 341 to about amino acid residue 447 of an IgG).

The term "hinge region" is generally defined as stretching from Glu216 to Pro230 of human IgG1 (Burton (1985). Hinge regions of other IgG isotypes may be aligned with the IgG1 sequence by placing the first and last cysteine residues forming inter-heavy chain S—S bonds in the same positions.

The term "binding domain" refers to the region of a polypeptide that binds to another molecule. In the case of an FcR, the binding domain can comprise a portion of a polypeptide chain thereof (e.g., the a chain thereof) which is responsible for binding an Fc region. One exemplary binding domain is the extracellular domain of an FcR chain.

A "functional Fc region" possesses at least a partial "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an antibody variable domain) and can be assessed using various assays as herein disclosed, for example.

A "native sequence Fc region" comprises an amino acid sequence identical to the amino acid sequence of an Fc region found in nature. A "variant Fc region" as appreciated by one of ordinary skill in the art comprises an amino acid sequence which differs from that of a native sequence Fc region by virtue of at least one "amino acid modification." Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and more preferably at least about 90% homology therewith, more preferably at least about 95% homology therewith, even more preferably, at least about 99% homology therewith.

The term "altered glycosylation" refers to a polypeptide, as defined above, be it native or modified, in which the carbohydrate addition to the heavy chain constant region is manipulated to either increase or decrease specific sugar components. For example, polypeptides, such as, for example, antibodies, prepared in specific cell lines, such as, for example, Lec2 or Lec3, may be deficient in the attachment of sugar moieties such as fucose and sialic acid.

The terms "Fc receptor" or "FcR" are used to describe a receptor that binds to the Fc region of an antibody. In one embodiment of the invention, FcR is a native sequence human FcR. In another embodiment, FcR, including human FcR, binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daron, $Annu\ Rev\ Immunol$, 15, 203-234 (1997); FcRs are reviewed in Ravetch and Kinet, $Annu\ Rev\ Immunol$, 9, 457-92(1991); Capel et al., $Immunomethods$, 4, 25-34 (1994); and de Haas et al., $J\ Lab\ Clin\ Med$, 126, 330-41 (1995), Nimmerjahn and Ravetch 2006, Ravetch Fc Receptors in Fundemental Immunology, ed William Paul $5^{th}$ Ed. each of which is incorporated herein by reference).

"Antibody-dependent cell-mediated cytotoxicity" and "ADCC" refer to an in vitro or in vivo cell-mediated reaction in which cytotoxic cells that express FcRs (e.g., monocytic cells such as natural killer (NK) cells and macrophages) recognize bound antibody on a target cell and subsequently cause lysis of the target cell. In principle, any effector cell with an activating FcR can be triggered to mediate ADCC. One such cell, the NK cell, expresses FcγRIII only, whereas monocytes, depending on their state of activation, localization, or differentiation, can express FcγRI, FcγRII, and FcγRIII. FcR expression on hematopoietic cells is summarized in Ravetch and Bolland, $Annu\ Rev\ Immunol$, (2001), which is incorporated herein by reference.

"Human effector cells" are leukocytes which express one or more FcRs and perform effector functions. Preferably, the cells express at least one type of an activating Fc receptor, such as, for example, FcγRIII and perform ADCC effector function. Examples of human leukocytes which mediate ADCC include peripheral blood mononuclear cells (PBMC), natural killer (NK) cells, monocytes, and neutrophils, with PBMCs and NK cells being preferred. The effector cells may be isolated from a native source thereof, e.g., from blood or PBMCs as described herein.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The phrase "sialic acid content" of an antibody refers both to the total number of sialic acid residues on an Fc region of a heavy chain of an antibody and to the ratio of sialylated antibodies to asialylated antibodies in an unpurified antibody preparation, unless the phrase is in a context clearly suggesting that another meaning is intended.

"Antibody fragments", as defined for the purpose of the present invention, comprise a portion of an intact antibody, generally including the antigen binding or variable region of the intact antibody or the Fc region of an antibody which retains FcR binding capability. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature, 256, 495-497 (1975), which is incorporated herein by reference, or may be made by recombinant DNA methods (see, e.g., U.S. Pat. No. 4,816,567, which is incorporated herein by reference). The monoclonal antibodies may also be isolated from phage antibody libraries using the techniques described in Clackson et al., $Nature$, 352, 624-628 (1991) and Marks et al., $J\ Mol\ Biol$, 222, 581-597 (1991), for example, each of which is incorporated herein by reference.

In other embodiments of the invention, the polypeptide containing at least one IgG Fc region may be fused with other protein fragments, including, without limitation, whole proteins. A person of ordinary skill in the art will undoubtedly appreciate that many proteins may be fused with the polypeptide of the present invention, including, without limitation, other immunoglobulins, especially, immunoglobulins lacking their respective Fc regions. Alternatively, other biologically active proteins or fragments thereof may be fused with the polypeptide of the present invention, as described, for example, in the U.S. Pat. No. 6,660,843, which is incorporated herein by reference. This embodiment is especially advantageous for delivery of such biologically active proteins or fragments thereof to cells expressing Fc receptors. Further, different markers, such as, for example, GST tag or green fluorescent protein, or GFP, may be used.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; Morrison et al., *Proc Natl Acad Sci USA,* 81, 6851-6855 (1984); Neuberger et al., *Nature,* 312, 604-608 (1984); Takeda et al., *Nature,* 314, 452-454 (1985); International Patent Application No. PCT/GB85/00392, each of which is incorporated herein by reference).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody optionally also will comprise at least a portion of an immunoglobulin constant region (Fc), typically that of a human immunoglobulin. For further details, see Jones et al., *Nature,* 321, 522-525 (1986); Riechmann et al., Nature, 332, 323-329 (1988); Presta, *Curr Op Struct Biol,* 2, 593-596 (1992); U.S. Pat. No. 5,225,539, each of which is incorporated herein by reference.

The polypeptides containing at least one IgG Fc region include those in which specific amino acid substitutions, additions or deletions are introduced into a parental sequence through the use of recombinant DNA techniques to modify the genes encoding the heavy chain constant region. The introduction of these modifications follows well-established techniques of molecular biology, as described in manuals such as Molecular Cloning (Sambrook and Russel, (2001)). In addition, the polypeptides with at least one Fc region will include those polypeptides which have been selected to contain specific carbohydrate modifications, obtained either by expression in cell lines known for their glycosylation specificity (Stanley P., et al., Glycobiology, 6, 695-9 (1996); Weikert S., et al., *Nature Biotechnology,* 17, 1116-1121 (1999); Andresen D C and Krummen L., *Current Opinion in Biotechnology,* 13, 117-123 (2002)) or by enrichment or depletion on specific lectins or by enzymatic treatment (Hirabayashi et al., *J Chromatogr B Analyt Technol Biomed Life Sci,* 771, 67-87 (2002); Robertson and Kennedy, *Bioseparation,* 6, 1-15 (1996)). It is known in the art that quality and extent of antibody glycosylation will differ depending on the cell type and culture condition employed. (For example, Patel et al., *Biochem J,* 285, 839-845 (1992)) have reported that the content of sialic acid in antibody linked sugar side chains differs significantly if antibodies were produced as ascites or in serum-free or serum containing culture media. Moreover, Kunkel et al., Biotechnol Prog, 16, 462-470 (2000) have shown that the use of different bioreactors for cell growth and the amount of dissolved oxygen in the medium influenced the amount of galactose and sialic acid in antibody linked sugar moieties. These studies, however, did not address how varying levels of sialic acid residues influence antibody activity in vivo.

Host Expression Systems

The polypeptide of the present invention can be expressed in a host expression systems, i.e., host cells, capable of N-linked glycosylation. Typically, such host expression systems may comprise bacterial, fungal, plant, vertebrate or invertebrate expression systems. In one embodiment the host cell is a mammalian cell, such as a Chinese hamster ovary (CHO) cell line, (e.g. CHO-K1; ATCC CCL-61), Green Monkey cell line (COS) (e.g. COS 1 (ATCC CRL-1650), COS 7 (ATCC CRL-1651)); mouse cell (e.g. NS/0), Baby Hamster Kidney (BHK) cell line (e.g. ATCC CRL-1632 or ATCC CCL-10), or human cell (e.g. HEK 293 (ATCC CRL-1573)), or any other suitable cell line, e.g., available from public depositories such as the American Type Culture Collection, Rockville, Md. Further, an insect cell line, such as a Lepidoptora cell line, e.g. Sf9, a plant cell line, a fungal cell line, e.g., yeast such as, for example, *Saccharomyces cerevisiae, Pichia pastoris, Hansenula* spp., or a bacterial expression system based on *Bacillus,* such as *B. subtilis,* or *Eschericiae coli* can be used. It will be appreciated by one of ordinary skill in the art that in some cases modifications to host cells may be required to insure that N-linked glycosylation and glycan maturation occur to result in a complex, biantennary sugar as typically found on the Fc domain of human IgG.

Therapeutic Formulations

Therapeutic formulations comprising the polypeptides containing at least one IgG Fc region can be prepared for storage by mixing the polypeptides of the present invention having the desired degree of purity with optional physiologically acceptable carriers, excipients or stabilizers (see, e.g., Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenyl, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In preferred embodiments, the formulations to be used for in vivo administration are sterile. The formulations of the instant invention can be easily sterilized, for example, by filtration through sterile filtration membranes.

Sustained-release preparations may also be prepared. Suitable examples of sustained-release preparations include semipermeable matrices of solid hydrophobic polymers containing the modified antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (see, e.g., U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Creation of sialylated polypeptides containing at least one IgG Fc region.

The polypeptides of the present invention can be further purified or modified so that they have an increased amount of sialic acid compared to unmodified and/or unpurified antibodies. Multiple methods exist to reach this objective. In one method, the source of unpurified polypeptides, such as, for example, IVIG, is passed through the column having lectin, which is known to bind sialic acid. A person of the ordinary skill in the art will appreciate that different lectins display different affinities for α2,6 versus α2,3 linkages between galactose and sialic acid. Thus, selecting a specific lectin will allow enrichment of antibodies with the desired type of linkage between the sialic acid and the galactose. In one embodiment, the lectin is isolated from *Sambuccus nigra*. A person of the ordinary skill in the art will appreciate that the *Sambuccus nigra* agglutinin (SNA) is specific for sialic acids linked to galactose or N-acetylgalactosamine by a(2-6) linkages. Shibuya et al, *J. Biol. Chem.*, 262: 1596-1601 (1987). In contrast, the *Maakia amurensis* ("MAA") lectin binds to sialic acid linked to galactose by a(2-3) linkages. Wang et al, *J Biol. Chem.*, 263: 4576-4585 (1988).

Thus, a fraction of the polypeptides containing at least one IgG Fc region having a desired linkage between the galactose and the sialic acid will be retained in the column while a fraction lacking such linkage will pass through. The sialylated fraction of the polypeptides containing at least one IgG Fc region can be eluted by another wash with a different stringency conditions. Thus, it is possible to obtain a preparation of the polypeptide of the present invention wherein the content of sialic acid is increased compared to the normal content. Further, one may employ an enzymatic reaction with a sialyltransferase and a donor of sialic acid as described, for example, in the U.S. Pat. No. 20060030521.

Suitable non-limiting examples of sialyltransferase enzymes useful in the claimed methods are ST3Gal III, which is also referred to as α-(2,3)sialyltransferase (EC 2.4.99.6), and α-(2,6)sialyltransferase (EC 2.4.99.1).

Alpha-(2,3)sialyltransferase catalyzes the transfer of sialic acid to the Gal of a Gal-β-1,3GlcNAc or Gal-β-1,4GlcNAc glycoside (see, e.g., Wen et al., J. Biol. Chem. 267: 21011 (1992); Van den Eijnden et al., J. Biol. Chem. 256: 3159 (1991)) and is responsible for sialylation of asparagine-linked oligosaccharides in glycopeptides. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., J. Biol. Chem. 257: 13845 (1982)); the human cDNA (Sasaki et al. (1993) J. Biol. Chem. 268: 22782-22787; Kitagawa & Paulson (1994) J. Biol. Chem. 269: 1394-1401) and genomic (Kitagawa et al. (1996) J. Biol. Chem. 271: 931-938) DNA sequences are known, facilitating production of this enzyme by recombinant expression.

Activity of α-(2,6)sialyltransferase results in 6-sialylated oligosaccharides, including 6-sialylated galactose. The name "α-(2,6)sialyltransferase" refers to the family of sialyltransferases attaching sialic acid to the sixth atom of the acceptor polysaccharide. Different forms of a-(2,6)sialyltransferase can be isolated from different tissues. For example, one specific form of this enzyme, ST6Gal II, can be isolated from brain and fetal tissues. Krzewinski-Recchi et al., *Eur. J. Biochem.* 270, 950 (2003).

In addition, a person of average skill in the art will appreciate that cell culture conditions can be manipulated to change the sialylation rate. For example, to increase the sialic acid content, production rate is decreased and osmolality is generally maintained within a lower margin suitable for the particular host cell being cultured. Osmolality in the range from about 250 mOsm to about 450 mOsm is appropriate for increased sialic acid content. This and other suitable cell culture conditions are described in, e.g., U.S. Pat. No. 6,656, 466. Patel et al., Biochem J, 285, 839-845 (1992) have reported that the content of sialic acid in antibody linked sugar side chains differs significantly if antibodies were produced as ascites or in serum-free or serum containing culture media. Moreover, Kunkel et al., *Biotechnol. Prog.*, 16, 462-470 (2000) have shown that the use of different bioreactors for cell growth and the amount of dissolved oxygen in the medium influenced the amount of galactose and sialic acid in antibody linked sugar moieties.

In another embodiment, host cells, such as, for example, immortalized human embryonic retina cells, may be modified by introducing a nucleic acid encoding a sialyltransferase such as, for example, an α-2,3-sialyltransferase or an α-2,6-sialyltransferase, operably linked to a promoter, such as, for example, a CMV promoter. The α-2,3-sialyltransferase may be the human α-2,3-sialyltransferase, known as SIAT4C or STZ (GenBank accession number L23767), and described, for example, in the U.S. Pat. No. 20050181359.

The nucleic acid encoding the sialyltransferase may be introduced into the host cell by any method known to a person of ordinary skill in the art. Suitable methods of introducing exogenous nucleic acid sequences are also described in Sambrook and Russel, *Molecular Cloning: A Laboratory Manual* (3rd Edition), Cold Spring Harbor Press, NY, 2000. These methods include, without limitation, physical transfer techniques, such as, for example, microinjection or electroporation; transfections, such as, for example, calcium phosphate transfections; membrane fusion transfer, using, for example, liposomes; and viral transfer, such as, for example, the transfer using DNA or retroviral vectors.

The polypeptide containing at least one IgG Fc region may be recovered from the culture supernatant and can be subjected to one or more purification steps, such as, for example, ion-exchange or affinity chromatography, if desired. Suitable methods of purification will be apparent to a person of ordinary skill in the art.

A person of ordinary skill in the art will appreciate that different combinations of sialylation methods, disclosed above, can lead to production of the polypeptides containing at least one IgG Fc region with an extremely high level of sialylation. For example, one can express the polypeptide containing at least one IgG Fc region in the host cells overexpressing sialyltransferase, as described above, and then further enrich the sialylated fraction of these polypeptides by, for example, sialylating these polypeptides in an enzymatic reaction followed by an affinity chromatography using lectin-containing columns. Similarly, an enzymatic reaction followed by affinity chromatography may be used for IVIG source of the polypeptides containing at least one IgG Fc region.

To examine the extent of glycosylation on the polypeptides containing at least one IgG Fc region, these polypeptides can be purified and analyzed in SDS-PAGE under reducing conditions. The glycosylzation can be determined by reacting the isolated polypeptides with specific lectins, or, alternatively as would be appreciated by one of ordinary skill in the art, one can use HPLC followed by mass spectrometry to identify the glycoforms. (Wormald, M R et al., Biochem 36:1370 (1997).

To describe the instant invention in more details, several non-limiting illustrative examples are given below.

EXAMPLES

Example 1

IVIG with Increased Sialic Acid Content Exhibits Decreased Cytotoxicity

To determine if specific glycoforms of IgG are involved in modulating the effector functions of antibodies the role of specific, $Asn^{297}$—linked carbohydrates in mediating the cytotoxicity of defined IgG monoclonal antibodies was explored. The anti-platelet antibodies, derived from the 6A6 hybridoma, expressed as either an IgG1, 2a or 2b switch variant in 293 cells as previously described (6), were analyzed by mass spectroscopy to determine their specific carbohydrate composition and structure. These antibodies contain minimal sialic acid residues. Enrichment of the sialic acid containing species by *Sambucus nigra* lectin affinity chromatography yielded antibodies enriched 60-80 fold in sialic acid content. Comparison of the ability of sialylated and asialylated 6A6-IgG1 and 2b antibodies to mediate platelet clearance revealed an inverse correlation between sialylation and in vivo activity. Sialylation of 6A6 IgG antibodies resulted in a 40-80% reduction in biological activity.

To determine the mechanism of this reduction in activity surface plasmon resonance binding was performed on these antibodies for each of the mouse FcγRs and to its cognate antigen.

Surface plasmon resonance analysis was performed as described in Nimmerjahn and Ravetch, *Science* 310, 1510 (2005). Briefly, 6A6 antibody variants containing high or low levels of sialic acid residues in their sugar side chains were immobilized on the surface of CM5 sensor chips. Soluble Fcγ-receptors were injected at different concentrations through flow cells at room temperature in HBS-EP running buffer (10mM Hepes, pH 7.4, 150 mM NaCl, 3.4 mM EDTA, and 0.005% surfactant P20) at a flow rate of 3μl/min. Soluble Fc-receptors were injected for 3 minutes and dissociation of bound molecules was observed for 7 minutes. Background binding to control flow cells was subtracted automatically. Control experiments were performed to exclude mass transport limitations. Affinity constants were derived from sensorgram data using simultaneous fitting to the association and dissociation phases and global fitting to all curves in the set. A 1:1 Langmuir binding model closely fitted the observed sensorgram data and was used in all experiments.

A 5-10 fold reduction in binding affinity was observed for the sialylated forms of these antibodies to their respective activating FcγRs as compared to their asialylated counterparts, while no differences in binding affinity for the antigen were observed. Since IgG2b binds with a higher affinity to its activation receptor, FcγRIV, when compared to IgG1 binding to its activation receptor FcγRIII, the effect of sialylation was to generate a binding affinity for IgG2b for its activation receptor FcγRIV that was comparable to that of asialylated IgG1 binding to its activation receptor FcγRIII. This effect of this quantitative difference in activation receptor binding resulted in sialylated IgG2b displaying an in vivo activity comparable to that of asialylated IgG1. Similarly, sialylation of IgG1 reduces its already low binding affinity for its activation receptor FcγRIII by a factor of 7 thereby generating a physiologically inactive antibody. Thus, sialylation of the $Asn^{297}$ linked glycan structure of IgG resulted in reduced binding affinities to the subclass-restricted activation FcγRs and thus reduced their in vivo cytotoxicity.

To determine the generality of the observation that sialylation of the N-linked glycan of IgG was involved in modulating its in vivo inflammatory activity, we next examined the role of N-linked glycans on the anti-inflammatory activity of IVIG. This purified IgG fraction obtained from the pooled serum of 5-10,000 donors, when administered intravenously at high doses (1-2 g/kg), is a widely used therapeutic for the treatment of inflammatory diseases. Dwyer, *N. Engl. J. Med.* 326, 107 (1992). This anti-inflammatory activity is a property of the Fc fragment and is protective in murine models of ITP, RA and nephrotoxic nephritis. Imbach et al., *Lancet* 1, 1228 (1981), Samuelsson et al., *Science* 291, 484 (2001), Bruhns et al., *Immunity* 18, 573 (2003), Kaneko et al., *J. Exp. Med.* in press (2006).

A common mechanism for this anti-inflammatory activity was proposed involving the induction of surface expression of the inhibitory FcγRIIB molecule on effector macrophages, thereby raising the threshold required for cytotoxic IgG antibodies or immune complexes to induce effector cell responses by activation FcγR triggering. Nimmerjahn and Ravetch, *Immunity* 24, 19 (2006).

Example 2

Asialylation of IVIG decreases the Anti-Inflammatory Effect of IVIG in Mouse Arthritis Model Mice C57BL/6 and NOD mice were purchased from the Jackson Laboratory (Bar Harbor, Me.). FcγRIIB$^{-/-}$ mice were generated in the inventors' laboratory and backcrossed for 12 generations to the C57BL/6 background. KRN TCR transgenic mice on a C57BU6 background (K/B) were gifts from D. Mathis and C. Benoist (Harvard Medical School, Boston, Mass.) and were bred to NOD mice to generate K/B×N mice. Female mice at 8-10 weeks of age were used for all experiments and maintained at the Rockefeller University animal facility. All experiments were done in compliance with federal laws and institutional guidelines and have been approved by the Rockefeller University (New York, N.Y.).

Antibodies and Soluble Fc Receptors

6A6 antibody switch variants were produced by transient transfection of 293T cells followed by purification via protein G as described. Nimmerjahn and Ravetch, *Science* 310, 1510 (2005). Sialic acid rich antibody variants were isolated from these antibody preparations by lectin affinity chromatography with *Sambucus nigra* agglutinin (SNA) agarose (Vector Laboratories, Burlingame, Calif.). Enrichment for sialic acid content was verified by lectin blotting (see below). Human intravenous immune globulin (IVIG, 5% in 10% maltose, chromatography purified) was purchased from Octapharma (Hemdon, Va.). Digestion of human IVIG was performed as described. Kaneko Y. et al., *Exp. Med.* in press (2006). Briefly, IVIG was digested by 0.5 mg/ml papain for 1 hr at 37° C., and stopped by the addition of 2.5 mg/ml iodoasetamide. Fab and Fc resulting fragments were separated from non-digested IVIG on a HiPrep 26/60 S-200HR column (GE Healthcare, Piscataway, N.J.), followed by purification of Fc and Fab fragments with a Protein G column (GE Healthcare) and a Protein L column (Pierce, Rockford, Ill.). Fragment purity was checked by immunoblotting using anti-human IgG Fab or Fc-specific antibodies. (Jackson ImmunoResearch, West Grove, Pa.). Purity was judged to be greater than 99%. The F4/80 antibody was from Serotec (Oxford, UK). The Ly 17.2 antibody was from Caltag (Burlingame, Calif.). Sheep anti-glomerular basement membrane (GBM) antiserum (nephrotoxic serum, NTS) was a gift from M. P. Madaio (University of Pennsylvania, Philadelphia, Pa.). Soluble Fc receptors containing a C-terminal hexa-hisitidine tag were generated by transient transfection of 293T cells and purified from cell culture supernatants with Ni-NTA agarose as suggested by the manufacturer (Qiagen).

IVIG was treated with neuraminidase and the composition and structure of the resulting preparation was analyzed by mass spectroscopy. No detectable sialic acid containing glycans remained after neuraminidase treatment. These IgG preparations were then tested for their ability to protect mice from joint inflammation induced by passive transfer of K×N serum, an IgG 1 immune complex-mediated inflammatory disease model. De-sialylation with neuraminidase abrogated the protective effect of the IVIG preparation in the K×N serum induced arthritis model. This loss of activity was not the result of reduced serum half-life of the asialylated IgG preparations or the result of changes to the monomeric composition or structural integrity of the IgG. Removal of all glycans with PNGase had a similar effect and abrogated the protective effect of IVIG in vivo.

Example 3

IVIG Fraction with Enriched Sialic Acid Content Decreases Inflammation in Mouse Arthritis Model Preparation of IVIG with an Increased Content of Sialic Acid Since sialic acid appeared to be required for the anti-inflammatory activity of IVIG, the basis for the high dose requirement (1 g/kg) for this anti-inflammatory activity could be the limiting concentration of sialylated IgG in the total IVIG preparation. The IVIG was fractionated on an SNA-lectin affinity column to obtain IgG molecules enriched for sialic acid modified glycan structures.

These sialic acid enriched fractions were tested for protective effects in the K×N serum transfer arthritis model as compared to unfractionated IVIG. A 10 fold enhancement in protection was observed for the SNA-binding fraction, such that equivalent protection was obtained at 0.1 g/kg of SNA-enriched IVIG as compared to 1 g/kg of unfractionated IVIG. The serum half-life and IgG subclass distribution of the SNA enriched fraction was equivalent to that of unfractionated IVIG. The effect of sialylation was specific to IgG; sialylated N-linked glycoproteins such as fetuin or transferrin with similar bi-antennary, complex carbohydrate structures had no statistically significant anti-inflammatory activity at equivalent molar concentrations of IgG. Finally, the mechanism of protection of the sialylated IVIG preparation was similar to unfractionated IVIG in that it was dependent on FcγRIIB expression and resulted in the increased expression of this inhibitory receptor on effector macrophages.

Example 4

The Increased Anti-Inflammatory Response of IVIG with Increased Sialic Acid Content is Mediated by Sialylation of the N-Linked Glycan on the Fc Domain Since the polyclonal IgG in IVIG may also contain O and N linked glycans on the light chains or heavy chain variable domains that can be sialylated, we confirmed that the increase in anti-inflammatory activity of the SNA-enriched IgG preparation resulted from increased sialylation of the N-linked glycosylation site on the Fc. Fc fragments were generated from unfractionated and SNA fractionated IVIG and tested for their in vivo activity. As observed for intact IgG, SNA-purified Fc fragments were enhanced for their protective effect in vivo when compared to Fc fragments generated from unfractionated IVIG. In contrast, Fab fragments displayed no anti-inflammatory activity in this in vivo assay. Thus, the high dose requirement for the anti-inflammatory activity of IVIG can be attributed to the minor contributions of sialylated IgG present in the total preparation. Enrichment of these fractions by sialic acid binding lectin chromatography consequently increased the anti-inflammatory activity.

These results using passive immunization of IgG antibodies indicated that the ability of IgG to switch from a pro-inflammatory to an anti-inflammatory species is influenced by the degree of sialylation of the N-linked glycan on the Fc domain.

Example 5

Increase of Anti-Inflammatory Activity, Mediated by Sialylation of IgG, Occurs During an Active Immune Response Murine Model for Goodpasture's Disease In this model, mice are first sensitized with sheep IgG together with adjuvant and four days later injected with a sheep anti-mouse glomerular basement membrane preparation (nephrotoxic serum, NTS). Briefly, mice were pre-immunized intraperitoneally with 200 µg of sheep IgG (Serotec) in CFA, followed by intravenous injection of 2.5 µl of NTS serum per gram of body weight four days later. Blood was collected from non-treated control mice four days after the anti-GBM anti-serum injection, and serum IgG was purified by Protein G (GE Healthcare, Princeton, N.J.) and sepharose-bound sheep IgG column, generated by covalently coupling sheep IgG on NHS-activated sepharose column (GE Healthcare, Princeton, N.J.), affinity chromatography.

Pre-sensitization followed by treatment with NTS induces mouse IgG2b anti-sheep IgG antibodies (NTN immunized). Kaneko Y. et al., *Exp. Med.*, 203:789 (2006). Mouse IgG2b antibodies are deposited in the glomerulus together with the NTS antibodies and result in an acute and fulminant inflammatory response by the IgG2b mediated activation of FcγRIV on infiltrating macrophages. In the absence of pre-sensitization inflammation is not observed, indicating that the mouse IgG2b anti-sheep IgG antibodies are the mediators of the inflammatory response.

To determine if active immunization resulting in pro-inflammatory IgG is associated with a change in sialylation, serum IgG and IgM from preimmune and NTS immunized mice were characterized for sialic acid content by SNA lectin binding. Total IgG sialylation was reduced on average by 40% in immunized mice as compared to the unimmunized controls. The effect was specific for IgG; sialylation of IgM was equivalent pre and post immunization. This difference in sialylation was more pronounced when the sheep specific IgG fraction from mouse serum was analyzed, showing a 50-60% reduction in sialylation compared to preimmune IgG.

These results were confirmed by MALDI-TOF-MS analysis. Monosaccharide composition analysis was performed by UCSD Glycotechnology Core Resource (San Diego, Calif.). Glycoprotein samples were denatured with SDS and 2-mercaptoethanol, and digested with PNGase F. The released mixed N-glycans were purified by reversed-phase HPLC and solid-phase extraction, and then exposed hydroxyl groups of the N-glycans were methylated. The resulting derivatized saccharides were purified again by reversed-phase HPLC and subject to MALDI-TOF-MS.

The analysis of the pre and post immunization IgGs confirmed that the changes in the N-glycan structure were specific to the terminal sialic acids moieties. The mouse IgG2b anti-sheep antibodies that were deposited in the glomeruli, previously shown to be responsible for engagement of the FcγRIV bearing, infiltrating macrophages displayed reduced sialic acid content as compared to the pre-immunized controls.

Example 6

Analysis of Linkages Between Sialic Acid and Galactose in IVIG

Figure 1A:
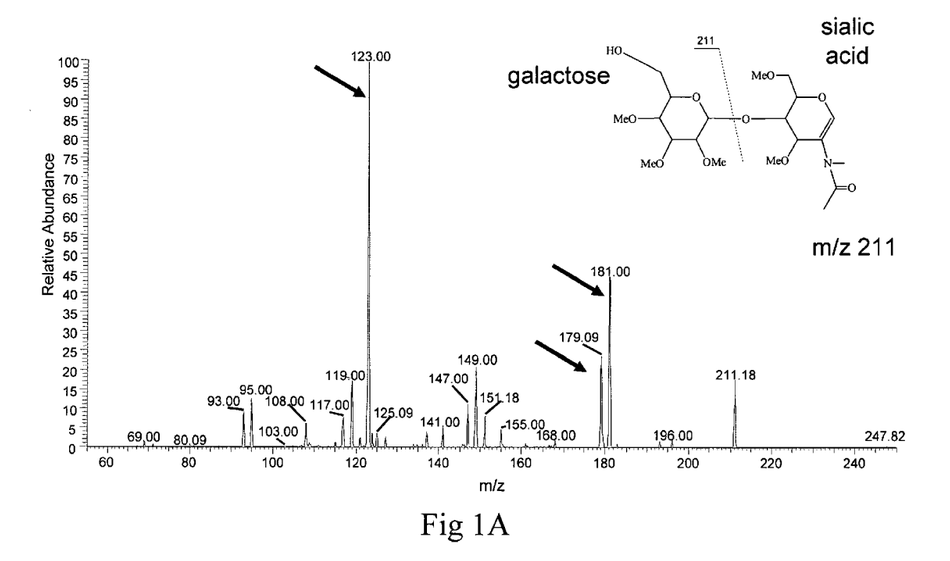
FIG. 1 is an illustration of MALDI-T of analysis of SNA+ FC linkages.
Figure 1B:
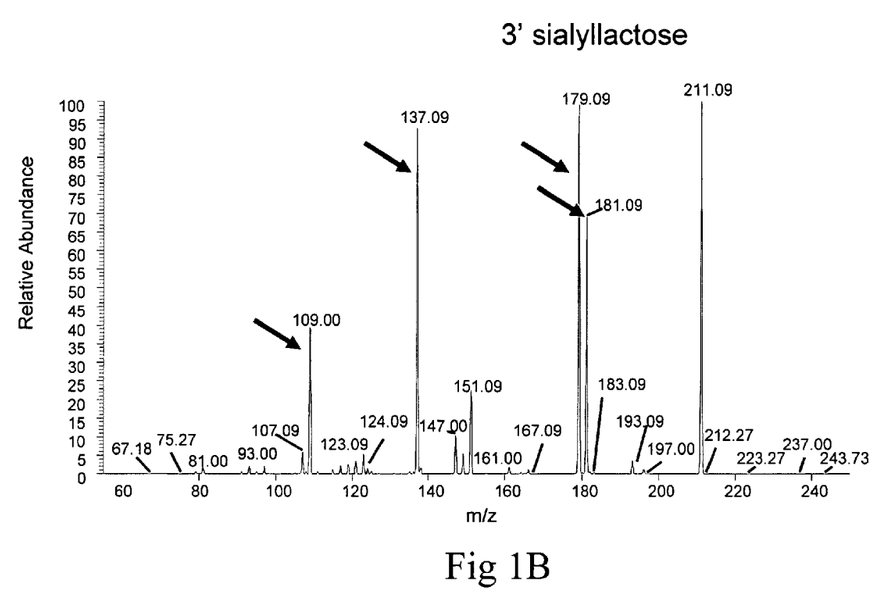
Figure 1C:
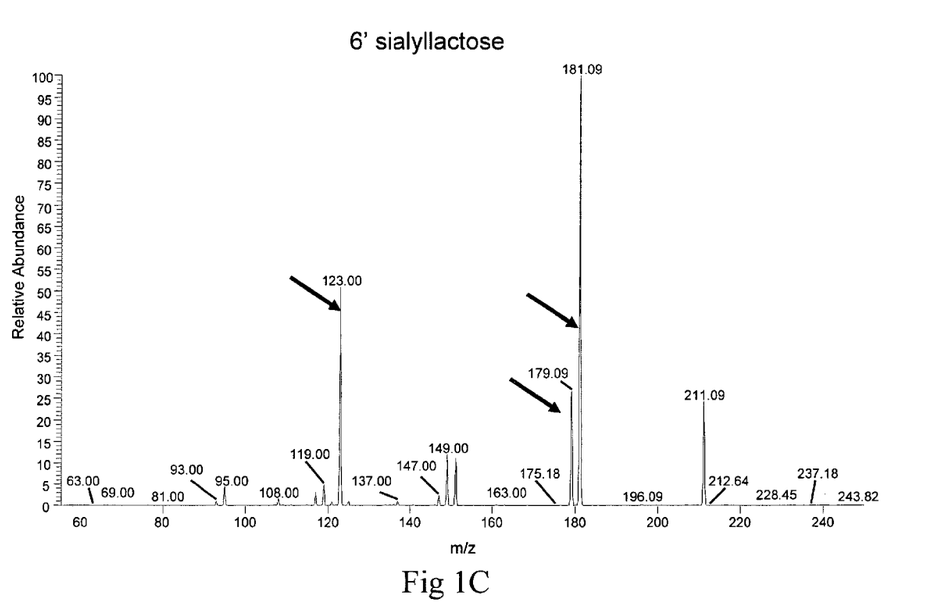

Sequential Maldi-Tof analysis of SNA+ (*Sambuccus Nigra* Agglutinin) IVIG Fc linkages was performed to determine the structure of the sialylated IgG Fc fraction that was protective in the ITP, RA and nephrotoxic nephritis models described above. Glycan peaks generated in Maldi-TOF were isolated, further fractionated, and reanalyzed until galactose-sialic acid structures were obtained. The footprint histogram of the enriched galactose-sialic acid structures with in vivo anti-inflammatory activity (FIG. 1A) were compared to histograms from sialic acid linkage standards, a2-3 sialyllactose (FIG. 1B) and a2-6 sialyllactose (FIG. 1C). The signature peaks of the standards are identified by arrows, shown by arrows for a2-3 (FIG. 1B) or a2-6 (FIGS. 1A and 1C), respectively, and compared to the peaks obtained from the sample.

Example 7

Figure 2:
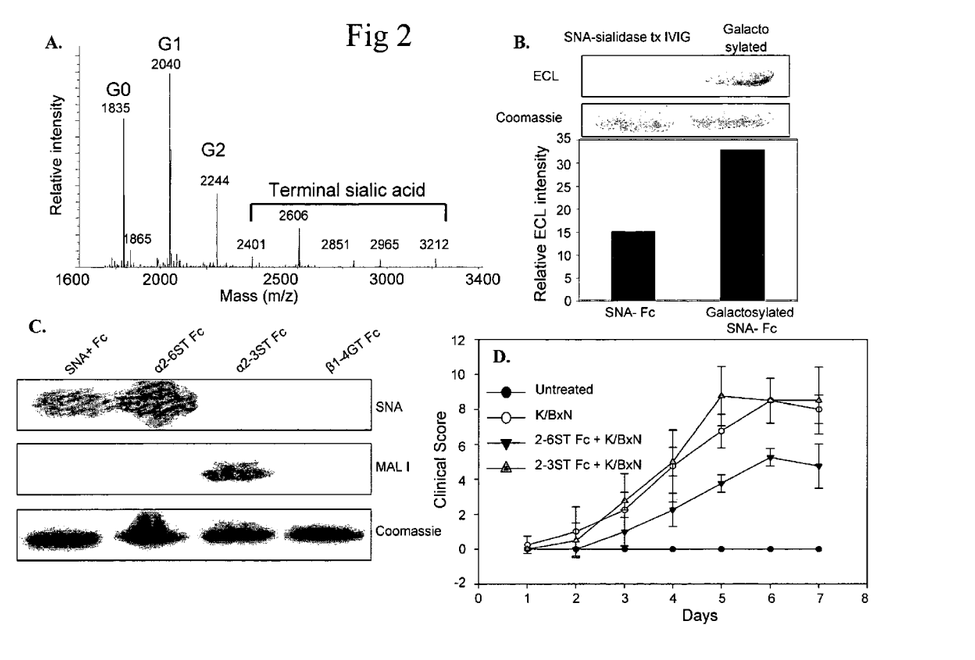
FIG. 2 summarizes experiments demonstrating that enrichment of α 2,6 linkages between sialic acid and galactose improves anti-inflammatory properties of IVIG Fc fragments.

Enrichment of IVIG Fc Fragments in α2,6 Linkages by In Vitro Glycosylation Improves Anti-Inflammatory Properties of IVIG As shown in FIG. 2A, glycan Maldi-T of MS analysis of IVIG Fc fragments showed structures ending in no galactose (peak G0), one galactose (peak G1), two galactose (peak G2), or in sialic acid (indicated by a bracket entitled "Terminal sialic acid"). To determine the in vivo activity of 2,3 or 2,6 sialylated IgG Fc, samples were treated with sialidase, followed by galactose transferase to convert the G0 (no galactose) and G1 (single_galactose) to G2 (fully galactosylated) to increase potential sialylation sites. As shown in FIG. 2B hypergalactosylation was verified by comparing relative band intensity ratios of terminal galactose as measured by ECL and coomassie loading controls. In vitro sialylation was performed (FIG. 2C) using either a 2-6 sialyltransferase ("ST6Gal") or a 2-3 sialyltransferase ("ST3Gal") and confirmed by lectin blotting for a 2-6 linkages with SNA (top) or a2-3 linkages with ECL (middle) and coomassie (bottom). To evaluate the ability of in vitro sialylated Fc to inhibit inflammation (FIG. 2D) mice received either 0.66 mg of a 2-6 sialylated Fcs (black triangles) or 0.66 mg a 2-3 sialylated Fcs (red triangles). 1 hour later, 0.2 ml of K/B×N sera was administered, and the swelling of footpads (clinical score) was monitored over the next seven days. Anti-inflammatory activity was observed for the 2,6 sialylated IgG Fc fragments but not for the 2,3 sialylated molecules. These results are consistent with the data shown above and indicate that a preferential linkage of 2,6 sialic acid-galactose is involved in the anti-inflammatory activity of sialylated IgG.

Example 8

Figure 3:
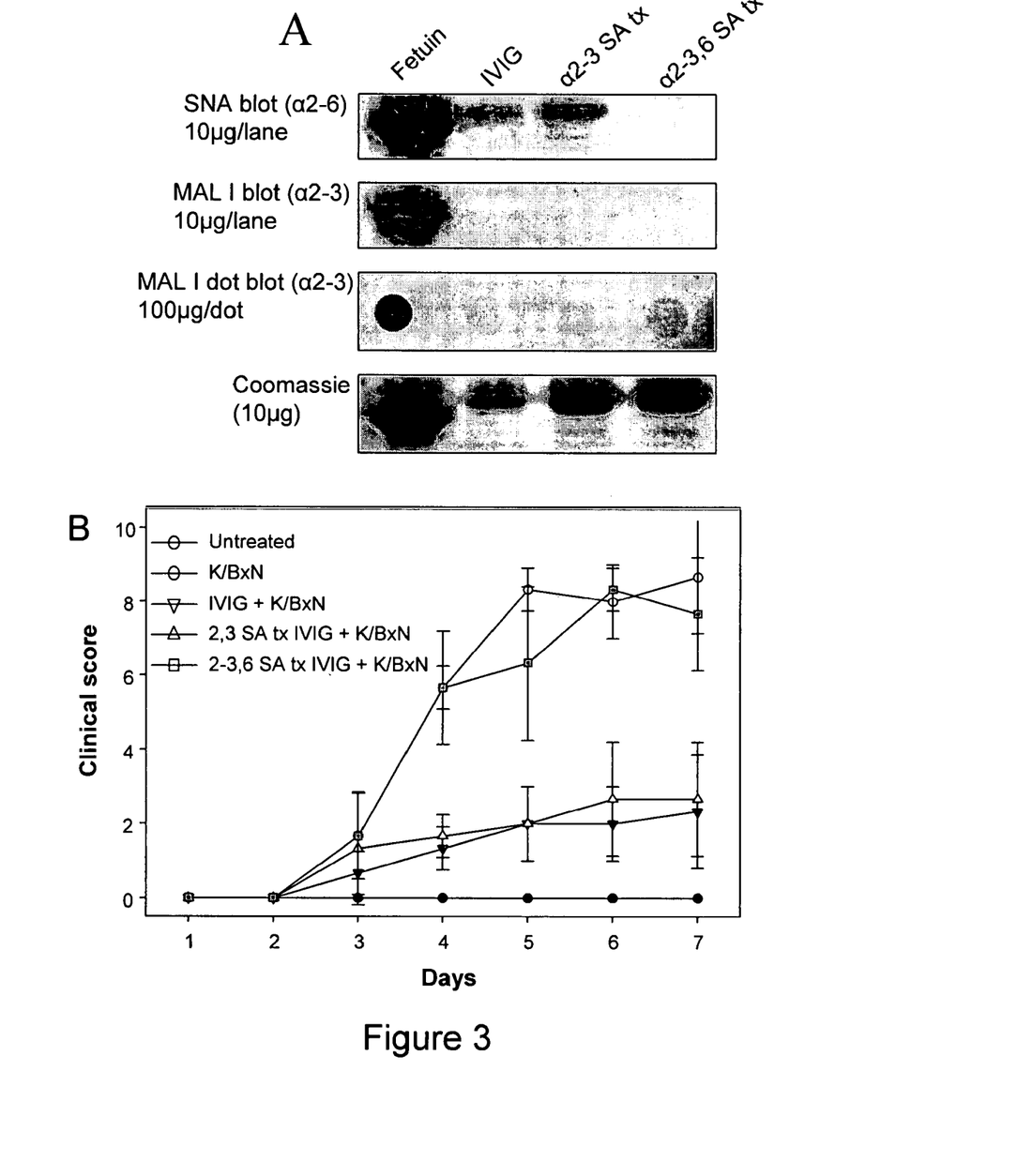
FIG. 3 summarizes experiments demonstrating that removal of α 2,6 linkages between sialic acid and galactose attenuates anti-inflammatory properties of IVIG Fc fragments.

Removal of a 2-6 but not 2,3 Sialic Acid Linkages Abrogates the Immunosuppressive Properties of IVIG IVIG was treated with linkage specific sialidases (SAs), and the digestion verified by lectin blotting (FIG. 3A). The top panel shows positive *Sambucus nigra* lectin (SNA) staining for a 2-6 linkages in IVIG (left lane), and a 2-3 SA tx IVIG (center lane), but not in a 2-3,6 SA tx IVIG (right lane). The middle panel is a dot blot for a2-3 sialic acid linkages (MAL I), displaying positive staining for the fetuin positive control only; 100 µg protein are loaded per dot. The bottom panel shows coomassie loading control. 10 µg/lane are shown in the blot and gel. To examine the effect of specific removal of sialic acid moieties, mice were given 1 g/kg of IVIG preparations prior to 200 µl of K/B×N sera. As shown in FIG. 3B, footpad swelling was observed in mice administered K/B×N sera (white circles) over the course of a week, as measured by clinical scoring. IVIG treated mice showed minimal swelling (black triangles), as did mice treated with a2-3 SA tx IVIG (white triangles), while mice receiving a2-3,6 SA tx IVIG (red squares) were not protected from footpad swelling.

All patent and non-patent publications cited in this disclosure are incorporated herein in to the extent as if each of those patent and non-patent publications was incorporated herein by reference in its entirety. Further, even though the invention herein has been described with reference to particular examples and embodiments, it is to be understood that these examples and embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method of inhibiting inflammation in a subject, comprising
   providing a purified preparation of IgG Fc regions from an IVIG source, wherein the purified preparation has (i) increased anti-inflammatory activity as compared to the IVIG source, and (ii) a higher content of α2,6 linked sialic acid in the N-linked glycans of the Fc regions than the IVIG source, and
   administering to a subject having inflammation a dose of the purified preparation sufficient to inhibit inflammation in the subject.

2. The method of claim 1, wherein the IgG Fc regions comprise one or more of human IgG1, IgG2, IgG3 or IgG4 Fc regions.

3. The method of claim 1, wherein the IgG Fc regions from the IVIG source are modified by treatment with α2-6 sialyltransferase.

4. The method of claim 1, wherein the IgG Fc regions from the IVIG source are purified from the IVIG source by using one or more of affinity chromatography HPLC, lectin affinity chromatography, high pH anion exchange chromatography, ion-exchange chromatography, and any combination thereof.

5. The method of claim 1, wherein the IgG Fc regions from the IVIG source are purified from the IVIG source by using a lectin having a higher affinity to α2,6 linkages than to α2,3 linkages between sialic acids and galactose.

6. The method of claim 1, wherein the subject has an inflammatory disease.

7. The method of claim 1, wherein the subject has arthritis, thrombocytopenia, or nephritis.

* * * * *

UNITED STATES PATENT AND TRADEMARK OFFICE
CERTIFICATE OF CORRECTION

PATENT NO. : 8,470,318 B2
APPLICATION NO. : 12/447204
DATED : June 25, 2013
INVENTOR(S) : Jeffrey Ravetch It is certified that error appears in the above-identified patent and that said Letters Patent is hereby corrected as shown below:

Title Page, Col. 1 item (75), (Inventors), line 2, delete "Thumau" and insert -- Thurnau --

Title Page, Col. 2 item (56), (Other Publications), line 29, delete ""Niger" and insert -- "Higher --

Title Page 2, Col. 1 item (56), (Other Publications), line 26, delete "Activatin" and insert -- Activation --

Title Page 2, Col. 1 item (56), (Other Publications), line 33, delete "relatd" and insert -- related --

Title Page 2, Col. 1 item (56), (Other Publications), line 41, delete "reeptor" and insert -- receptors --

Title Page 2, Col. 1 item (56), (Other Publications), line 41, delete "dendiritic" and insert -- dendritic --

Title Page 2, Col. 2 item (56), (Other Publications), line 1, delete "Identifrication" and insert -- Identification --

Title Page 2, Col. 2 item (56), (Other Publications), line 9, delete "Rocekfeller" and insert -- Rockefeller --

Title Page 2, Col. 2 item (56), (Other Publications), line 11, delete "compelment" and insert -- complement --

Title Page 2, Col. 2 item (56), (Other Publications), line 14, delete "involvment" and insert -- involvement --

Signed and Sealed this
Eighth Day of October, 2013

Teresa Stanek Rea
*Deputy Director of the United States Patent and Trademark Office*

CERTIFICATE OF CORRECTION (continued)
U.S. Pat. No. 8,470,318 B2

Title Page 2, Col. 2 item (56), (Other Publications), line 23, delete "Activiating" and insert
-- Activating --

Title Page 2, Col. 2 item (56), (Other Publications), line 26, delete "hmolog" and insert -- homolog --